(12) United States Patent
Li et al.

(10) Patent No.: US 10,743,789 B2
(45) Date of Patent: Aug. 18, 2020

(54) ECG SIGNAL PARALLEL ANALYSIS APPARATUS, METHOD AND MOBILE TERMINAL

(71) Applicant: SHENZHEN INSTITUTES OF ADVANCED TECHNOLOGY, CHINESE ACADEMY OF SCIENCES, Shenzhen, Guangdong (CN)

(72) Inventors: Ye Li, Guangdong (CN); Xiaomao Fan, Guangdong (CN); Yunpeng Cai, Guangdong (CN); Qihang Yao, Guangdong (CN); Yujie Yang, Guangdong (CN)

(73) Assignee: SHENZHEN INSTITUTES OF ADVANCED TECHNOLOGY, CHINESE ACADEMY OF SCIENCES, Shenzhen (CN)

( * ) Notice: Subject to any disclaimer, the term of this patent is extended or adjusted under 35 U.S.C. 154(b) by 138 days.

(21) Appl. No.: 15/739,719

(22) PCT Filed: Nov. 28, 2017

(86) PCT No.: PCT/CN2017/113408
§ 371 (c)(1),
(2) Date: Dec. 23, 2017

(87) PCT Pub. No.: WO2019/100417
PCT Pub. Date: May 31, 2019

(65) Prior Publication Data
US 2019/0150778 A1    May 23, 2019

(30) Foreign Application Priority Data
Nov. 21, 2017 (CN) .......................... 2017 1 1169664

(51) Int. Cl.
*A61B 5/0452* (2006.01)
*A61B 5/04* (2006.01)
(Continued)

(52) U.S. Cl.
CPC ........ *A61B 5/04525* (2013.01); *A61B 5/0022* (2013.01); *A61B 5/0404* (2013.01);
(Continued)

(58) Field of Classification Search
CPC .............. A61B 5/04525; A61B 5/0022; A61B 5/01012; A61B 5/0404; A61B 5/0472;
(Continued)

(56) References Cited

U.S. PATENT DOCUMENTS 10,258,250 B2 * 4/2019 Li ...................... A61B 5/04017

* cited by examiner

*Primary Examiner* — Paula J Stice

(57) ABSTRACT

Provided are an electrocardiogram signal parallel analysis apparatus, a mobile terminal incorporating the apparatus, and related methods. The apparatus includes an integrated memory, a central processing unit and a graphic processing unit. The integrated memory includes a first memory and a second memory for being used by the central processing unit and the graphic processing unit respectively, and the central processing unit may access the second memory. The central processing unit performs primary noise reduction on a received electrocardiogram original signal to obtain a primary electrocardiogram signal, and performs abnormal heartbeat classification preliminary screening on characteristic data extracted from the graphic processing unit to obtain suspected abnormal heartbeat data. The graphic processing unit performs characteristic extraction on the primary electrocardiogram signal to obtain characteristic data, performs secondary noise reduction on the primary electrocardiogram signal to obtain a secondary electrocardiogram signal, and processes the suspected abnormal heartbeat data (Continued)

and the secondary electrocardiogram signal by applying a template matching classification mode to obtain final abnormal heartbeat data.

16 Claims, 3 Drawing Sheets

(51) Int. Cl.
    *A61B 5/0472* (2006.01)
    *A61B 5/00* (2006.01)
    *A61B 5/0404* (2006.01)
    *G16H 50/20* (2018.01)
    *A61B 5/0432* (2006.01)
    *A61B 5/0245* (2006.01)
    *A61B 5/0456* (2006.01)

(52) U.S. Cl.
    CPC ........ *A61B 5/04012* (2013.01); *A61B 5/0472* (2013.01); *G16H 50/20* (2018.01); *A61B 5/0006* (2013.01); *A61B 5/0245* (2013.01); *A61B 5/0456* (2013.01); *A61B 5/04325* (2013.01); *A61B 5/7203* (2013.01)

(58) Field of Classification Search
    CPC . A61B 5/0006; A61B 5/04325; A61B 5/7203; G16H 50/20
    See application file for complete search history.

ECG SIGNAL PARALLEL ANALYSIS APPARATUS, METHOD AND MOBILE TERMINAL

CROSS-REFERENCE TO RELATED APPLICATION

This application is a § 371 National Stage Application of PCT/CN2017/113408, which was filed on Nov. 28, 2017, and claims priority to the Chinese patent application with the filing No. 2017111696640, filed with the State Intellectual Property Office on Nov. 21, 2017, and entitled "ECG Signal Parallel Analysis Apparatus, Method and Mobile Terminal", content of which is incorporated herein by reference in its entirety.

TECHNICAL FIELD

Present disclosure concerns to the technical field of electrocardiography signal processing, particularly concerns to an ECG signal parallel analysis apparatus, method and a mobile terminal.

BACKGROUND ART

ECG (Electrocardiogram), which may display the evolution of cardiac electrical activity over time, is one of the important physiological data. Heart rate, rhythm disorders, or morphological changes of electrocardiosignals may be pathological indicators. By analyzing the recorded ECG waveform, myocardial infarction, cardiomyopathy, myocarditis and various other heart diseases may be detected.

In order to monitor long-term ECG signals, a high-performance server is required to provide computing services. When a user submits an enormous amount of electrocardiogram analysis requests simultaneously in an unstable network environment, real-time response is difficult for the traditional cloud platform-based ECG signal analysis. If the analysis task of ECG signals is transferred to the mobile terminal, due to the limited CPU (Central Processing Unit) performance of the mobile terminal, it is still difficult to handle long-term ECG signal processing and make timely feedback. Meanwhile, since the processing needs to consume a large amount of power of the apparatus, for a mobile terminal with limited battery capacity, the battery losses are larger.

SUMMARY

In view of this, it is an object of the present disclosure to provide an ECG signal parallel analysis apparatus, method and a mobile terminal, to improve the analysis efficiency for ECG signals so as to improve the timeliness of the analysis feedback of ECG signals.

In order to achieve the above object, the technical solutions adopted in the present disclosure are as follows.

In a first aspect, the present disclosure provides a parallel analysis apparatus of an ECG signal, including: an integrated memory, a CPU and a GPU, wherein the integrated memory includes a first memory for being used by the CPU and a second memory for being used by the GPU, and the CPU may access the second memory; the CPU and the GPU are configured to transmit data via the integrated memory; the CPU is used for performing primary noise reduction processing on a received ECG original signal to obtain a primary ECG signal, and used for performing abnormal heartbeat classification preliminary screening process on characteristic data extracted from the GPU to obtain suspected abnormal heartbeat data; and the GPU is used for performing characteristic extraction on the primary ECG signal to obtain the characteristic data, and used for performing secondary noise reduction processing on the primary ECG signal to obtain a secondary ECG signal, and processing the suspected abnormal heartbeat data and the secondary ECG signal by using a template matching classification mode, to obtain final abnormal heartbeat data.

With reference to the first aspect, an embodiment of the present disclosure provides a first possible example of the first aspect, wherein the CPU includes an original signal reception module configured for receiving an ECG original signal and storing the ECG original signal in the first memory; a first pre-process module configured for performing primary noise reduction processing on the ECG original signal loaded from the first memory for primary noise reduction processing to obtain a primary ECG signal, and storing the primary ECG signal in the second memory; and a first abnormal heartbeat classification module configured for acquiring characteristic data according to storage location information, performing, in accordance with a set rule decision mode, an abnormal heartbeat classification on the characteristic data to obtain suspected abnormal heartbeat data, and storing the suspected abnormal heartbeat data in the second memory.

With reference to the first possible example of the first aspect, an embodiment of the present disclosure provides a second possible example of the first aspect, wherein the GPU includes: a characteristic detection module configured for performing characteristic extraction on the primary ECG signal loaded from the second memory to obtain characteristic data, and storing the characteristic data in the second memory; a second pre-process module configured for performing secondary noise reduction processing on the loaded primary ECG signal to obtain a secondary ECG signal; and a second abnormal heartbeat classification module configured for acquiring the secondary ECG signal from the second pre-process module, acquiring the suspected abnormal heartbeat data from the second memory, reconfirming, in accordance with a set template matching mode and based on the secondary ECG signal, the suspected abnormal heartbeat data to obtain final abnormal heartbeat data, and storing the final abnormal heartbeat data in the second memory.

With reference to the second possible example of the first aspect, an embodiment of the present disclosure provides a third possible example of the first aspect, wherein the integrated memory includes: a mapping module, configured for mapping storage location information of the characteristic data and the final abnormal heartbeat data to the first memory, so as to enable the CPU to acquire corresponding data according to the storage location information.

With reference to the second possible example of the first aspect, an embodiment of the present disclosure provides a fourth possible example of the first aspect, wherein the first pre-process module includes an IIR filter configured for performing filter processing on the ECG original signal to obtain a primary ECG signal; and the second pre-process module includes an artifact removal unit, configured for performing an artifact removal process on the primary ECG signal, to obtain a secondary ECG signal.

With reference to the second possible example of the first aspect, an embodiment of the present disclosure provides a fifth possible example of the first aspect, wherein the characteristic detection module includes: a morphology transformation unit configured for performing transformation on the primary ECG signal and outputting an ECG signal in a morphological form; an R wave detection unit configured for performing R wave detection on the ECG signal in a morphological form and outputting a detection result; and a QRS complex (QRS wave group) detection unit configured for performing QRS complex detection on the detection result and outputting characteristic data containing QRS complex.

In a second aspect, the present disclosure provides a method of parallel analysis of an ECG signal, which is applied to a mobile terminal, wherein the mobile terminal includes: an integrated memory, a CPU and a GPU, the integrated memory includes a first memory for being used by the CPU and a second memory for being used by the GPU, and the CPU may access the second memory; the CPU and the GPU are configured to transmit data via the integrated memory, wherein the method includes: the CPU performing primary noise reduction processing on a received ECG original signal to obtain a primary ECG signal, the GPU performing characteristic extraction on the primary ECG signal to obtain characteristic data, the CPU performing abnormal heartbeat classification preliminary screening process on the characteristic data to obtain suspected abnormal heartbeat data, the GPU performing secondary noise reduction processing on the primary ECG signal to obtain a secondary ECG signal, and processing the suspected abnormal heartbeat data and the secondary ECG signal by using a template matching classification mode to obtain final abnormal heartbeat data.

With reference to the second aspect, an embodiment of the present disclosure provides a first possible example of the second aspect, wherein the method also includes: the CPU acquiring the final abnormal heartbeat data and uploading the final abnormal heartbeat data to a remote medical platform; and the CPU receiving a report fed back by the medical platform based on the final abnormal heartbeat data.

With reference to the second aspect or the first possible example of the second aspect, an embodiment of the present disclosure provides a second possible example of the second aspect, wherein a process of the CPU and GPU transmitting data via the integrated memory includes: the integrated memory copying the data stored by the CPU in the first memory to the second memory, and mapping storage location information of the data stored by the GPU in the second memory to the first memory.

In a third aspect, the present disclosure provides a mobile terminal that includes the above-described ECG signal parallel analysis apparatus.

According to embodiments of the present disclosure, there are provided an ECG signal parallel analysis apparatus, method, and a mobile terminal, wherein the integrated memory includes a first memory for being used by the CPU and a second memory for being used by the GPU; the final abnormal heartbeat data is obtained by performing, by the CPU, primary noise reduction processing on an ECG original signal and performing an abnormal heartbeat classification preliminary screening process on characteristic data extracted from the GPU, performing, by the GPU, characteristic extraction on the primary ECG signal obtained by the primary noise reduction process, performing secondary noise reduction processing on the primary ECG signal, and then processing suspected abnormal heartbeat data obtained by the preliminary screening processing and the secondary ECG signal obtained by the secondary noise reduction process by applying a template matching classification mode. In this method, the CPU and GPU co-process various tasks in the ECG signal analysis process, the GPU completes complicated calculation tasks in parallel processing mode, improving the analysis efficiency for the ECG signal and thereby improving the timeliness of the analysis and feedback of the ECG signal. Meanwhile, equipment power consumption is reduced and user experience is improved.

Further, the above way of data replication and mapping between memories can avoid a large amount of data transmission and reduce the data transmission time from the CPU side to the GPU side, compared with the way of data transmission through buses and the communication lines, further improving the efficiency of ECG signal analysis.

Other features and advantages of the present disclosure will be set forth in the following description, or, part of the features and advantages may be inferred or undoubtedly determined from the specification, or may be learned by implementing of above techniques of the present disclosure.

The above objects, features and advantages of the present disclosure will become more apparent from the following detailed description of preferred embodiments thereof, taken in conjunction with the accompanying figures.

BRIEF DESCRIPTION OF DRAWINGS

To describe the technical solutions in the embodiments of the present disclosure or in the prior art more clearly, accompanying figures required for describing the embodiments or the prior art are introduced below briefly. Obviously, the accompanying figures in the following description show some embodiments of the present disclosure, and persons of ordinary skill in the art may still derive other drawings from these accompanying drawings without creative efforts.

DETAILED DESCRIPTION OF EMBODIMENTS

To make the objectives, technical solutions, and advantages of the disclosed embodiments more comprehensible, the technical solutions of the present disclosure will be described clearly and completely with reference to the accompanying figures. Apparently, the described embodiments are only some of embodiments of the present disclosure rather than all embodiments. All other embodiments obtained by a person skilled in the art based on the embodiments of the present disclosure without creative efforts shall fall within the protection scope of the present disclosure.

Long-term ECG may be used to help diagnosis of heart diseases such as intermittent cardiac arrhythmia. A user may acquire the ECG signal through a wearable heart monitoring device and send the ECG signal to a cloud platform connected with the device, with the cloud platform analyzing and diagnosing the ECG signal and then feeding back the diagnosis result to the monitoring device or the user's mobile terminal. Due to volume of ECG signal data is large and the cloud platform may continuously receive ECG signals sent from a large number of users, the way of the cloud platform processing the ECG signal poses a large computational burden to the cloud processor, resulting in that the feedback timeliness and reliability of ECG signal processing cannot be guaranteed.

In order to alleviate the above problems, the tasks of ECG signal analysis and diagnosis can be completed by a mobile terminal such as a wearable heart monitoring device, a mobile phone and a tablet computer, etc.; however, due to the limited CPU performance of the mobile terminal, it is still difficult to handle long-term ECG signal processing and timely make feedback; at the same time, the processing needs to consume a larger amount of power of the device, and the battery loss is larger for a mobile terminal with limited battery capacity.

In view of the problem of slow feedback of the ECG signal analysis method described above, the embodiments of the present disclosure provide an ECG signal parallel analysis apparatus, method and a mobile terminal. The technology can be applied to wearable heart monitoring devices, cell phones, tablet computers and the like mobile terminals, and used in the scene of assisting the diagnosis of intermittent cardiac arrhythmias and other heart diseases. The technology can be implemented by related software or hardware, and is described below by ways of embodiment.

Figure 1:
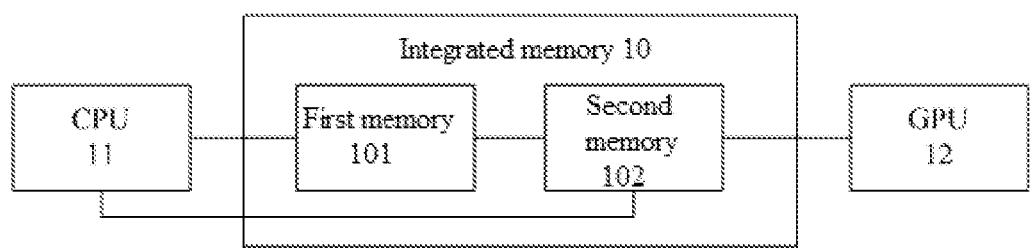
FIG. 1 is a schematic structural diagram of an ECG signal parallel analysis apparatus according to an embodiment of the present disclosure.

Referring to a schematic structural diagram of an ECG signal parallel analysis apparatus shown in FIG. 1, the apparatus includes: an integrated memory 10, a CPU 11 and a Graphic Processing Unit (GPU) 12. The integrated memory 10 includes a first memory 101 for being used by the CPU 11 and a second memory 102 for being used by the GPU 12, and the CPU 11 can access the second memory 102. The CPU 11 and the GPU 12 transmit data via the integrated memory 10.

The CPU 11 is used for performing primary noise reduction processing on a received ECG original signal to obtain a primary ECG signal; and used for performing abnormal heartbeat classification preliminary screening on characteristic data extracted from the GPU 12 to obtain suspected abnormal heartbeat data.

The GPU 12 is used for performing characteristic extraction on the primary ECG signal to obtain the characteristic data; and used for performing secondary noise reduction processing on the primary ECG signal to obtain a secondary ECG signal, and processing the suspected abnormal heartbeat data and the secondary ECG signal by using a template matching classification mode to obtain final abnormal heartbeat data.

The above CPU and GPU are respectively used to perform different tasks in ECG signal analysis, wherein some tasks may be performed in parallel. For example, when the CPU performs an abnormal heartbeat classification preliminary screening process, the GPU may perform a secondary noise reduction process on the primary ECG signal. Besides, due to the large amount of tasks undertaken by the CPU, the execution of tasks with complicated computations of the CPU is weak, and the GPU, which adopts a multi-core processing manner, can handle in parallel the computationally complicated tasks such as image computation, etc. or algorithms with inherent parallel features. According to the attributes of the task, it can improve the efficiency of ECG signal analysis by reasonably distributing the processors for performing the task. For example, the above characteristic extraction step, which usually requires image recognition, calculation, etc. and requires a large amount of computation, is performed by the GPU, which can greatly improve the efficiency of ECG signal analysis.

Above integrated memory may be implemented by using an memory chip, wherein the first memory and the second memory may be divided in a form of software; the first memory can be used to store an ECG original signal, a primary ECG signal, and suspected abnormal heartbeat data and other data; and the second memory can be used to store a primary ECG signal, characteristic data, suspected abnormal heartbeat data, and final abnormal heartbeat data and other data.

Data transmission between the first memory and the second memory may be performed by copying and mapping. For example, the integrated memory may copy, to the second memory, the data stored by the CPU in the first memory and map, to the first memory, the memory location information of the data stored by the GPU in the second memory. Specifically, because the CPU can access both the first memory and the second memory, when the CPU needs to acquire the data in the second memory, only the storage address of the data in the second memory needs to be mapped to the first memory, the CPU accesses the second memory according to the mapped storage address, and obtains corresponding data. Since the GPU can only access the second memory, when the GPU needs to acquire the data in the first memory, the integrated chip needs to copy the data from the first memory into the second memory and then the data is read by the GPU.

According to an embodiment of the present disclosure, there is provided an ECG signal parallel analysis apparatus, wherein the integrated memory includes a first memory for being used by the CPU and a second memory for being used by the GPU. The final abnormal heartbeat data is obtained by performing, by the CPU, primary noise reduction processing on an ECG original signal and performing abnormal heartbeat classification preliminary screening on characteristic data extracted from the GPU, performing, by the GPU, characteristic extraction on the primary ECG signal obtained by the primary noise reduction process, performing secondary noise reduction on the primary ECG signal, and processing suspected abnormal heartbeat data obtained by the preliminary screening process and the secondary ECG signal obtained by the secondary noise reduction process by using a template matching classification mode. In this manner, the CPU and GPU co-process various tasks in the ECG signal analysis process, and the GPU completes complicated calculation tasks in parallel processing mode, improving the analysis efficiency for the ECG signal and thereby improving the timeliness of the analysis and feedback of the ECG signal. Meanwhile, equipment power consumption is reduced and user experience is improved.

Further, the above way of data replication and mapping between memories can avoid a large amount of data transmission and reduce the data transmission time from the CPU side to the GPU side, compared with the way of data transmission through the buses and the communication lines, further improving the efficiency of ECG signal analysis.

Figure 2:
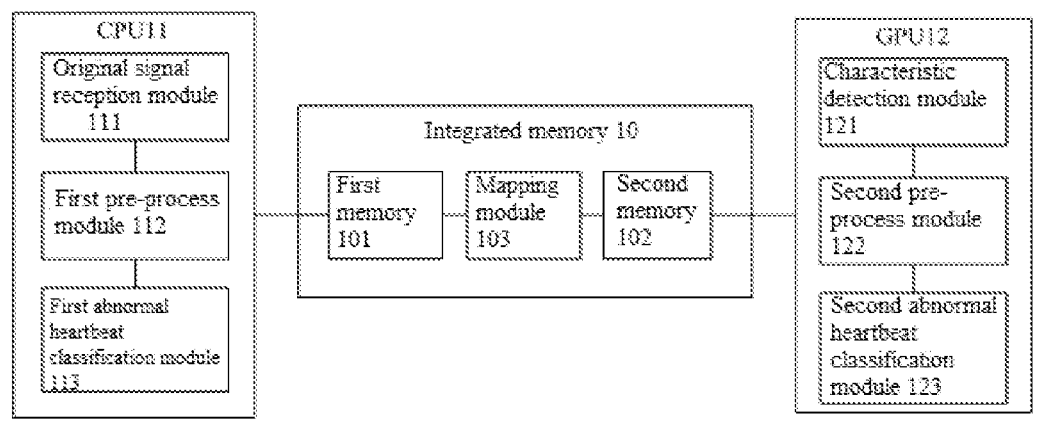
FIG. 2 is a schematic structural diagram of another ECG signal parallel analysis apparatus according to an embodiment of the present disclosure.

Referring to the schematic structural diagram of another ECG signal parallel analysis apparatus shown in FIG. 2, the apparatus is implemented on the basis of the apparatus shown in FIG. 1. The apparatus includes an integrated memory 10, a CPU 11 and a GPU 12. The integrated memory 10 includes the first memory 101 for being used by the CPU 11, and the second memory 102 for being used by the GPU 12, and the CPU 11 can access the second memory 102. The CPU 11 and the GPU 12 transmit data via the integrated memory 10.

Mobile terminals such as smartphones have highly integrated circuits that combine major components (such as CPU, GPU, memory, etc.) into a single chip. This approach enables high-bandwidth data transmission; and at the same time, the ultra-bandwidth memory indicator accelerates the speed of data transmission between the memory and the CPU/GPU. In addition, the CPU and GPU memories are integrated on the same chip, and separated by embedded software. Tasks are transferred during task execution, so memory-mapping techniques can be introduced to map the same piece of physical memory into the memory spaces of the CPU and GPU to reduce or even avoid data transmission.

The CPU specifically includes: an original signal reception module 111 configured for receiving an ECG original signal and storing the ECG original signal in the first memory; a first pre-process module 112 configured for performing primary noise reduction processing on the ECG original signal loaded from the first memory for to obtain a primary ECG signal, and storing the primary ECG signal in the second memory; a first abnormal heartbeat classification module 113 configured for acquiring characteristic data according to storage location information, performing, in accordance with a set rule decision mode, abnormal heartbeat classification on characteristic data to obtain suspected abnormal heartbeat data, and storing suspected abnormal heartbeat data in the second memory.

The original signal reception module can be connected with an electrocardiogram sensor; and the electrocardiogram sensor can sense the action potential waveform of cells in different regions of the heart and convert it into a signal that can be output, wherein the signal is the ECG original signal.

The first pre-process module may include an Infinite Impulse Response (IIR) filter configured for filter processing the ECG original signal to obtain a primary ECG signal. Of course, the filter processing may also be implemented by other filters, such as a Finite Impulse Response (FIR) filter. Due to the tightly coupled mode of the IIR filter, parallelization is difficult to achieve, so the IIR filter is implemented in the CPU. After the first pre-process module processes and obtains the primary ECG signal, the primary ECG signal is usually first stored in the first memory; and because the subsequent characteristic extraction process is performed by the GPU, the integrated memory copies the primary ECG signal to the second memory, for acquisition by the GPU.

The first abnormal heartbeat classification module may acquire a predefined rule determination mode from the first memory. The rule determination mode may be implemented as a parameter threshold. For example, if one or more parameters in the characteristic data are greater than corresponding threshold values, it can be initially determined that there is abnormality of the ECG signal; the type of the abnormality may also be preliminarily classified according to the threshold values to obtain the suspected abnormal heartbeat data, and then the suspected abnormal heartbeat data may be saved again. The suspected abnormal heartbeat data processed and obtained by the first abnormal heartbeat classification module is usually firstly stored into the first memory; and since the subsequent re-confirmation processing of the suspected abnormal heartbeat data is performed by the GPU, the integrated memory copies the classification results to the second memory for acquisition by the GPU.

The GPU specifically includes: a characteristic detection module 121 configured for performing characteristic extraction on the primary ECG signal loaded from the second memory to obtain characteristic data, and storing the characteristic data in the second memory; a second pre-process module 122 configured for performing secondary noise reduction processing on the loaded primary ECG signal to obtain a secondary ECG signal; a second abnormal heartbeat classification module 123 configured for acquiring the secondary ECG signal from the second pre-process module, acquiring suspected abnormal heartbeat data from the second memory, reconfirming, in accordance with a set template matching mode and based on the secondary ECG signal, the suspected abnormal heartbeat data to obtain final abnormal heartbeat data, and storing the final abnormal heartbeat data in the second memory.

The above-mentioned characteristic detection module can be implemented by various characteristic extraction algorithms, such as machine learning, wavelet transformation, morphological transformation, etc. In view of the particularity of the ECG signal, in order to balance the accuracy and high efficiency of ECG signal characteristic recognition, the present embodiment is specifically implemented in the following manner: specifically, the characteristic detection module includes: (1) a morphology transformation unit, configured for performing transformation on the primary ECG signal, and outputting an ECG signal in morphological form; (2) an R wave detection unit, configured for performing R wave detection on the ECG signal in a morphological form, and outputting a detection result; and (3) a QRS complex detection unit, configured for performing QRS complex detection on the detection result, and outputting characteristic data containing QRS complex.

In the ECG signal, an R wave is a positive wave firstly appears in a signal period and located above a reference horizontal line. The QRS complex includes an R wave, a Q wave, an S wave, an R' wave, an S' wave and a QS wave. By detecting parameters of width, time internal, amplitude, shape and so on of these waveforms, a variety of characteristic data may be obtained.

The characteristic data extracted by the characteristic detection module is usually stored in the second memory. Although the CPU can access the second memory, position of the data stored in the second memory needs to be mapped to the first memory. Based on this, the integrated memory includes a mapping module 103 configured for mapping storage location information of the characteristic data and the final abnormal heartbeat data to the first memory, so as to enable the CPU to acquire corresponding data according to a storage location information. This manner makes the CPU be able to more quickly obtain the data processed and obtained by the GPU, avoiding the time-consuming data transmission, thereby improving the analysis efficiency for the ECG signal.

The second pre-process module may include an artifact removal unit configured for performing artifact removal on a primary ECG signal to obtain a secondary ECG signal. In general, the signal detected by a sensor from a body surface electrode contains different types of interference, such as power frequency interference, baseline drift, electrode contact noise, electromyography interference, and movement interference and so on, these interference forming artifacts in the ECG signal. In order to obtain relatively pure ECG signals so as to improve the accuracy of subsequent characteristic detection and heartbeat abnormity recognition, the present embodiment adopts above artifact removal unit to perform artifact removal processing on the primary ECG signal.

The second abnormal heartbeat classification module acquires the secondary ECG signal from the second pre-process module on one hand and acquires the suspected abnormal heartbeat data from the second memory on the other hand, and the suspected abnormal heartbeat data is in advance copied from the first memory to the second memory; the second abnormal heartbeat classification module generates a QRS standard template from a secondary ECG signal of a noise-free signal, and then corrects the data of erroneous determination of the suspected abnormal heartbeat data according to the standard template to generate final abnormal heartbeat data. The final abnormal heartbeat data is saved to the second memory, and the address of the final abnormal heartbeat data in the second memory is mapped to the first memory for acquisition by the CPU. After the CPU acquires the final abnormal heartbeat data, the data may be pushed to a user terminal, uploaded to a cloud platform, or subjected to other processing.

Besides, the ECG signal parallel analysis apparatus may also be further optimized through workgroup size, data vectorization operation and zero memory copy technology, improving the efficiency of the analysis.

In the above manners, the CPU and the GPU co-process various tasks in ECG signal analysis process, and the GPU complete complex computing tasks in a parallel processing manner, improving the efficiency of ECG signal analysis, thereby improving the timeliness of ECG signal analysis and feedback. Meanwhile, the device power consumption is reduced, and user experience is improved.

Figure 3:
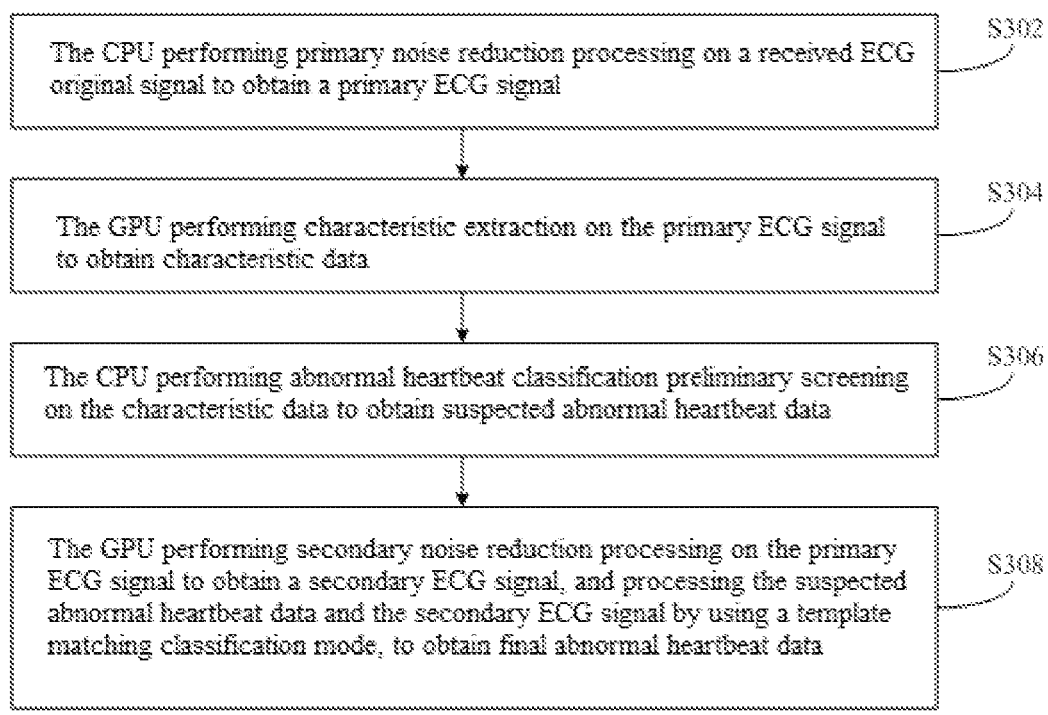
FIG. 3 is a flow chart of an ECG signal parallel analysis method according to an embodiment of the present disclosure.

Corresponding to the embodiments of the apparatuses, referring to a flow chart of an ECG signal parallel analysis method shown in FIG. 3, the method is applied to a mobile terminal. The mobile terminal includes: an integrated memory, a CPU and a GPU, wherein the integrated memory includes a first memory for being used by the CPU and a second memory for being used by the GPU, and the CPU may access the second memory; and the CPU and the GPU transmit data via the integrated memory. The method includes the following steps:

Step S302, the CPU performing primary noise reduction processing on a received ECG original signal to obtain a primary ECG signal;

Step S304, the GPU performing characteristic extraction on the primary ECG signal to obtain characteristic data;

Step S306, the CPU performing abnormal heartbeat classification preliminary screening on the characteristic data to obtain suspected abnormal heartbeat data; and Step S308, the GPU performing secondary noise reduction processing on the primary ECG signal to obtain a secondary ECG signal, and processing the suspected abnormal heartbeat data and the secondary ECG signal by using a template matching classification mode, to obtain final abnormal heartbeat data.

In the ECG signal parallel analysis method according to the embodiment of the present disclosure, the CPU performs primary noise reduction processing on the ECG original signal, and the GPU performs characteristic extraction on the primary ECG signal obtained by the primary noise reduction processing; the CPU performs abnormal heartbeat classification preliminary screening on extracted characteristic data, and the GPU performs secondary noise reduction processing on the primary ECG signal, and then processes, by applying a template matching classification mode, suspected abnormal heartbeat data obtained by the preliminary screening and a secondary ECG signal obtained by the secondary noise reduction, to obtain final abnormal heartbeat data. In this manner, the CPU and the GPU co-process various tasks in the ECG signal analysis process, and the GPU completes complicated calculation tasks in parallel processing mode, improving the analysis efficiency of the ECG signal and thereby improving the timeliness of the analysis and feedback of the ECG signal, and meanwhile reducing equipment power consumption and improving user experience.

Figure 4:
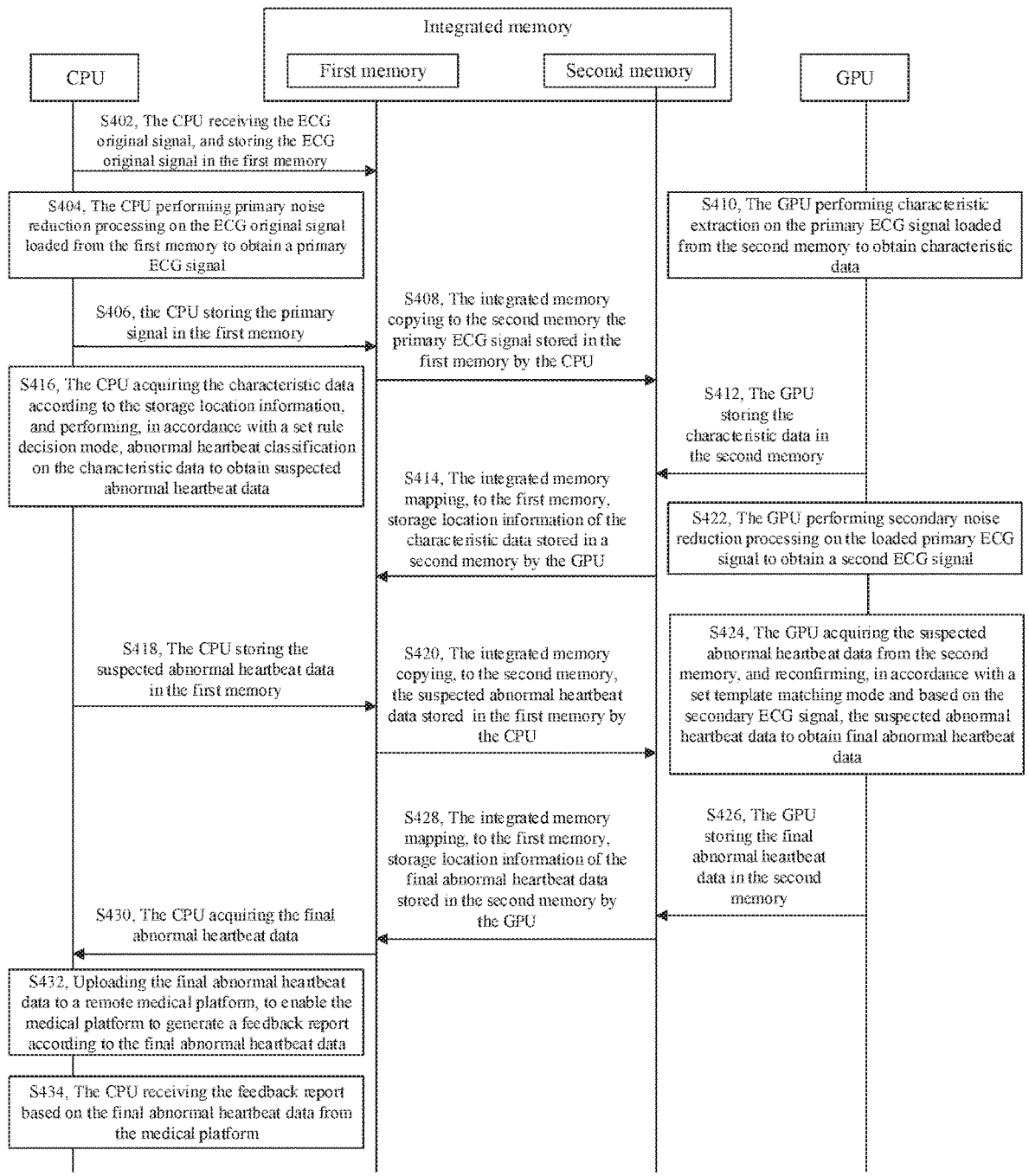
FIG. 4 is a flow chart of another ECG signal parallel analysis method according to an embodiment of the present disclosure.

Referring to a flow chart of another ECG signal parallel analysis method shown in FIG. 4, this method is implemented based on the method shown in FIG. 3. The method is implemented by multi-party interaction between a CPU of a mobile terminal, a first memory and a second memory in an integrated memory, and a GPU, wherein the second memory may also be referred to as a video memory. The method includes the following steps:

Step S402, the CPU receives an ECG original signal, and stores the ECG original signal in the first memory;

Step S404, the CPU loads the ECG original signal in the first memory for primary noise reduction processing to obtain a primary ECG signal;

Step S406, the CPU stores the primary ECG signal in the first memory;

Step S408, the integrated memory copies to a second memory the primary ECG signal stored by the CPU in the first memory;

Step S410, the GPU loads the primary ECG signal from the second memory for characteristic extraction to obtain characteristic data;

Step S412, the GPU stores the characteristic data in the second memory;

Step S414, the integrated memory maps to the first memory storage location information of the characteristic data stored by the GPU in a second memory;

Step S416, the CPU acquires the characteristic data according to the storage location information, and performs, in accordance with a set rule decision mode, abnormal heartbeat classification on the characteristic data to obtain suspected abnormal heartbeat data;

Step S418, the CPU stores the suspected abnormal heartbeat data in the first memory;

Step S420, the integrated memory copies, to the second memory, suspected abnormal heartbeat data stored by the CPU in the first memory;

Step S422, the GPU loads the primary ECG signal for secondary noise reduction processing, to obtain a secondary ECG signal; and in order to make full use of the heterogeneous computing resources of the CPU and the GPU, in this method, the secondary noise reduction process for removing artifacts of the ECG signal is adjusted from before the characteristic extraction to before the abnormal heartbeat re-confirmation;

Step S424, the GPU acquires the suspected abnormal heartbeat data from the second memory, and reconfirming, in accordance with a set template matching mode and based on the secondary ECG signal, the suspected abnormal heartbeat data, to obtain final abnormal heartbeat data;

Step S426, the GPU stores the final abnormal heartbeat data in the second memory;

Step S428, the integrated memory maps, to the first memory, storage location information of the final abnormal heartbeat data stored by the GPU in the second memory;

Step S430, the CPU acquires the final abnormal heartbeat data;

Step S432, the final abnormal heartbeat data is uploaded to a remote medical platform, to enable the medical platform to generate a feedback report according to the final abnormal heartbeat data; and Step S434, the CPU receives the feedback report based on the final abnormal heartbeat data from the medical platform.

In the above manner, the CPU and the GPU co-process various tasks in the ECG signal analysis process, and the GPU completes complicated calculation tasks in parallel processing mode, improving the analysis efficiency for the ECG signal and thus improving the timeliness of the analysis and feedback of the ECG signal, and meanwhile reducing equipment power consumption and improving user experience.

Corresponding to the above apparatus and method embodiments, an embodiment of the present disclosure further provides a mobile terminal, which includes the above ECG signal parallel analysis apparatus.

The ECG signal parallel analysis apparatus, method and mobile terminal provided by the embodiments of the present disclosure propose a new automatic ECG parallel analysis manner based on the Mobile Graphics processing unit (GPU), wherein compared with the sequential analysis manner of ECG signals, in the parallel manner, the whole program flow is reorganize and the CPU/GPU heterogeneous computing resources are fully utilized. This manner can significantly shorten the ECG data execution time of 24 hours, wherein through optimization in aspects of data vectorization, work group resizing and zero memory copy and others, the above execution time is further reduced, the feedback efficiency is improved, and the user experience is improved. Besides, when a large amount of computation is distributed to the GPU, the average power consumption of the test mobile device is small, alleviating the problem of limited battery working life of the mobile device.

In the several embodiments provided in the present disclosure, it should be understood that the disclosed apparatuses and methods may also be implemented in other manners. The apparatus embodiments described above are merely illustrative, for example, the flowchart and block diagrams in the figures illustrate the system structures, functions, and operations of possible implementations of apparatuses, methods and computer program products according to various embodiments of the present disclosure. In this regard, each block of the flowcharts or block diagrams may represent a module, a section of a program, or a portion of a code, and the module, section of a program, or portion of a code includes one or more executable instructions for implementing the specified logic functions. It should also be noted that in some alternative implementations, the functions marked in the blocks may occur in an order different from that marked in the figures. For example, two consecutive blocks may in fact be executed substantially in parallel, and sometimes they may be executed in the reverse order, depending on the function involved. It is also to be noted that each block of the block diagrams and/or flowcharts, and combinations of blocks in the block diagrams and/or flowcharts can be implemented by special hardware-based systems that perform the specified functions or actions, or can be implemented by a combination of dedicated hardware and computer instructions.

Besides, each function module or unit in the embodiments of the present disclosure may be integrated together to form an independent part, or the modules may exist separately, or two or more modules may be integrated to form an independent part.

The function, if implemented in the form of a software functional unit and sold or used as a separate product, may be stored in a computer-readable storage medium. Based on this understanding, the technical solutions of the present disclosure essentially, or the contributing parts to the prior art, or part of the technical solutions may be embodied as a software product, with the computer software product stored in a storage medium and including several instructions used to enable a computer device (may be a personal computer, a server, or a network device, etc.) to execute all or part of the steps of the method according to the embodiments of the present disclosure. The foregoing storage medium includes various media capable of storing program codes, such as a USB flash disk, a removable hard disk, a read-only memory (ROM), a random access memory (RAM), a magnetic disk, or an optical disk, etc.

Finally it should be noted that the above embodiments are merely specific implementations of the present disclosure for illustrating the technical solutions of the present disclosure rather than limiting the present disclosure, the protection scope of the present disclosure is not limited thereto, although the present disclosure has been described in detail with reference to the foregoing embodiments, those skilled in the art should understand: anyone skilled in the art may still make modifications to the technical solutions described in the foregoing embodiments or easily conceivable variations within the technical scope disclosed in the present disclosure, or replace some of the technical features equivalently; yet these modifications, variations or substitutions do not make the essence of the corresponding technical solutions depart from the spirit and scope of the technical solutions of the embodiments of the present disclosure, and should all fall within the protection scope of the present disclosure. Therefore, the protection scope of the present disclosure should be subject to the protection scope of the claims.

The invention claimed is:

1. An electrocardiogram signal parallel analysis apparatus, wherein the apparatus comprises an integrated memory, a central processor and a graphic processor, wherein the integrated memory is coupled to the central processor and to the graphic processor and comprises a first memory configured for being used by the central processor and a second memory configured for being used by the graphic processor, the central processor is configured to be able to access the second memory, and the central processor and the graphic processor are configured to transmit data via the integrated memory;

the central processor is configured for performing primary noise reduction processing on a received electrocardiogram original signal to obtain a primary electrocardiogram signal, and configured for performing abnormal heartbeat classification preliminary screening on characteristic data extracted by the graphic processor to obtain suspected abnormal heartbeat data: and the graphic processor is configured for performing characteristic extraction on the primary electrocardiogram signal to obtain the characteristic data, and configured for performing secondary noise reduction processing on the primary electrocardiogram signal to obtain a secondary electrocardiogram signal, and processing the suspected abnormal heartbeat data and the secondary electrocardiogram signal by using a template matching classification mode, to obtain final abnormal heartbeat data.

2. The apparatus according to claim 1, wherein the central processor is configured to perform the following operations:

receiving the electrocardiogram original signal and storing the electrocardiogram original signal in the first memory;

performing primary noise reduction processing on the electrocardiogram original signal loaded from the first memory, to obtain the primary electrocardiogram signal, and storing the primary signal in the second memory; and acquiring the characteristic data according to storage location information, performing, in accordance with a set rule decision mode, abnormal heartbeat classification on the characteristic data to obtain suspected abnormal heartbeat data, and storing the suspected abnormal heartbeat data in the second memory.

3. The apparatus according to claim 2, wherein the graphic processor is configured to perform the following operations:
performing characteristic extraction on the primary electrocardiogram signal loaded from the second memory to obtain characteristic data, and storing the characteristic data in the second memory;
performing secondary noise reduction processing on the loaded primary electrocardiogram signal to obtain the secondary electrocardiogram signal; and.
acquiring the secondary electrocardiogram signal from the second pre-process module to obtain the suspected abnormal heartbeat data from the second memory, reconfirming, in accordance with a set template matching mode and based on the secondary electrocardiogram signal, the suspected abnormal heartbeat data to obtain the final abnormal heartbeat data, and storing the final abnormal heartbeat data in the second memory.

4. The apparatus according to claim 3, wherein the integrated memory is further configured for mapping storage location information of the characteristic data and the final abnormal heartbeat data to the first memory, so as to enable the central processor to acquire corresponding data according to the storage location information.

5. The apparatus according to claim 3, wherein the operation of performing primary noise reduction processing on the electrocardiogram original signal loaded from the first memory to obtain the primary electrocardiogram original signal comprises performing filter processing on the electrocardiogram original signal to obtain the primary electrocardiogram signal; and
the operation of performing secondary noise reduction processing on the loaded primary electrocardiogram signal to obtain the secondary electrocardiogram signal comprises performing artifact removal processing on the primary electrocardiogram signal to obtain the secondary electrocardiogram signal.

6. The apparatus according to claim 3, wherein the operation of performing characteristic extraction on the primary electrocardiogram signal loaded from the second memory to obtain the characteristic data comprises:
performing transformation on the primary electrocardiogram signal, and outputting an electrocardiogram signal in a morphological form;
performing R wave detection on the electrocardiogram signal in a morphological form, and outputting a detection result; and
performing QRS complex detection on the detection result, and outputting characteristic data containing QRS complex.

7. An electrocardiogram signal parallel analysis method, applied to a mobile terminal, the mobile terminal comprising: an integrated memory, a central processor and a graphic processor, wherein the integrated memory is coupled to the central processor and to the graphic processor and comprises a first memory configured for being used by the central processor and a second memory configured for being used by the graphic processor, the central processor is configured to be able to access the second memory, and the central processor and the graphic processor are configured to transmit data via the integrated memory; and
the method comprises:
the central processor performing primary noise reduction processing on a received electrocardiogram original signal to obtain a primary electrocardiogram signal;
the graphic processor performing characteristic extraction on the primary electrocardiogram signal to obtain characteristic data;
the central processor performing abnormal heartbeat classification preliminary screening on the chara.cteristic data to obtain suspected abnormal heartbeat data; and
the graphic processor performing secondary noise reduction processing on the primary electrocardiogram signal to obtain a secondary electrocardiogram signal, and processing the suspected abnormal heartbeat data and the secondary electrocardiogram signal by using a template matching classification mode to obtain final abnormal heartbeat data.

8. The method according to claim 7, wherein the method further comprises:
the central processor acquiring the final abnormal heartbeat data, and uploading the final abnormal heartbeat data to a remote medical platform; and
the central processor receiving a report fed back by the medical platform based on the final abnormal heartbeat data.

9. The method according to claim 8, wherein a process of the central processor and the graphic processor transmitting data via the integrated memory comprises:
the integrated memory copying, to the second memory, data stored by the central processor in first memory, and mapping, to the first memory, storage location information stored by the graphic processor in the second memory.

10. The method according to claim 7, wherein a process of the central processor and the graphic processor transmitting data via the integrated memory comprises:
the integrated memory copying, to the second memory, data stored by the central processor in first memory, and mapping, to the first memory, storage location information stored by the graphic processor in the second memory.

11. A mobile terminal, comprising an electrocardiogram signal parallel analysis apparatus, wherein the apparatus comprises an integrated memory, a central processor and a graphic processor, wherein the integrated memory is coupled to the central processor and to the graphic processor and comprises a first memory configured for being used by the central processor and a second memory configured for being used by the graphic processor, the central processor is configured to be able to access the second memory, and the central processor and the graphic processor are configured to transmit data via the integrated memory;
the central processor is configured for performing primary noise reduction processing on a received electrocardiogram original signal to obtain a primary electrocardiogram signal, and configured for performing abnormal heartbeat classification preliminary screening on characteristic data extracted by the graphic processor to obtain suspected abnormal heartbeat data: and
the graphic processor is configured for performing characteristic extraction on the primary electrocardiogram signal to obtain the characteristic data, and configured for performing secondary noise reduction processing on the primary electrocardiogram signal to obtain a secondary electrocardiogram signal, and processing the suspected abnormal heartbeat data and the secondary electrocardiogram signal by using a template matching classification mode, to obtain final abnormal heartbeat data.

12. The mobile terminal according to claim 11, wherein the central processor is configured to perform the following operations:

receiving the electrocardiogram original signal and storing the electrocardiogram original signal in the first memory;

performing primary noise reduction processing on the electrocardiogram original signal loaded from the first memory, to obtain the primary electrocardiogram signal, and storing the primary signal in the second memory; and acquiring the characteristic data according to storage location information, performing, in accordance with a set rule decision mode, abnormal heartbeat classification on the characteristic data to obtain suspected abnormal heartbeat data, and storing the suspected abnormal heartbeat data in the second memory.

13. The mobile terminal according to claim 12, wherein the graphic processor is configured to perform the following operations:

performing characteristic extraction on the primary electrocardiogram signal loaded from the second memory obtain characteristic data, and storing the characteristic data in the second memory;

performing secondary noise reduction processing on the loaded primary electrocardiogram signal to obtain the secondary electrocardiogram signal; and acquiring the secondary electrocardiogram signal from the second pre-process module to obtain the suspected abnormal heartbeat data from the second memory, reconfirming, in accordance with a set template matching mode and based on the secondary electrocardiogram signal, the suspected abnormal heartbeat data to obtain the final abnormal heartbeat data, and storing the final abnormal heartbeat data in the second memory.

14. The mobile terminal according to claim 13, wherein the integrated memory is further configured for mapping storage location information of the characteristic data and the final abnormal heartbeat data to the first memory, so as to enable the central processor to acquire corresponding data according to the storage location information.

15. The mobile terminal according to claim 13, wherein the operation of performing primary noise reduction processing on the electrocardiogram original signal loaded from the first memory to obtain the primary electrocardiogram original signal comprises performing filter processing on the electrocardiogram original signal to obtain the primary electrocardiogram signal; and the operation of performing secondary noise reduction processing on the loaded primary electrocardiogram signal to obtain the secondary electrocardiogram signal comprises performing artifact removal processing on the primary electrocardiogram signal to obtain the secondary electrocardiogram signal.

16. The mobile terminal according to claim 13, wherein the operation of performing characteristic extraction on the primary electrocardiogram signal loaded from the secondary memory to obtain the characteristic data comprises:

performing transformation on the primary electrocardiogram signal, and outputting an electrocardiogram signal in a morphological form;

performing R wave detection on the electrocardiogram signal in a morphological form, and outputting a detection result; and performing QRS complex detection on the detection result, and outputting characteristic data containing QRS complex.

* * * * *